United States Patent [19]

Rout et al.

[11] Patent Number: 4,546,108

[45] Date of Patent: Oct. 8, 1985

[54] PESTICIDAL COMPOSITION AND USE

[75] Inventors: Ivan P. Rout, Bishops Stortford; Christopher Gillings, Linton, both of England

[73] Assignee: FBC Limited, Cambridge, England

[21] Appl. No.: 222,879

[22] Filed: Jan. 6, 1981

[30] Foreign Application Priority Data

Jan. 18, 1980 [GB] United Kingdom ............... 8001748

[51] Int. Cl.$^4$ ............................................. A01N 43/16
[52] U.S. Cl. ................................................... 514/464
[58] Field of Search ............................. 424/282, 280; 260/340.5 R

[56] References Cited

U.S. PATENT DOCUMENTS

| | | | |
|---|---|---|---|
| 2,951,850 | 9/1960 | Hartle et al. | 424/282 |
| 3,074,998 | 1/1963 | Whetstone et al. | 424/282 |
| 3,310,467 | 3/1967 | Kramer et al. | 424/282 |
| 3,736,338 | 5/1973 | Gates et al. | 424/282 |
| 4,171,372 | 10/1979 | Haynes et al. | 424/282 |
| 4,305,957 | 12/1981 | Drabek et al. | 424/282 |

*Primary Examiner*—Albert T. Meyers
*Assistant Examiner*—John W. Rollins, Jr.
*Attorney, Agent, or Firm*—Wenderoth, Lind & Ponack

[57] ABSTRACT

A stable liquid formulation of the pesticide bendiocarb, especially for ultra low volume application, comprises the bendiocarb suspended in a chemically inert oil of low volatility and of low solubility for bendiocarb.

16 Claims, No Drawings

PESTICIDAL COMPOSITION AND USE

This invention relates to a new formulation of bendiocarb.

Bendiocarb, 2,2-dimethyl-1,3-benzodioxol-4-yl methylcarbamate, is a know pesticide active for instance against insects. Pesticides are advantageously formulated as liquids so that the formulation can be sprayed on the locus to be treated, or readily measured out and diluted for spraying on the locus to be treated. Thus, pesticides are commonly formulated as emulsifiable concentrates, which are solutions of pesticides and surface active agents in organic solvents, the concentrates in use being diluted with water for spraying. If the pesticide is sufficiently soluble in water, it may be formulated as an aqueous solution. Bendiocarb, however, is not sufficiently soluble in water or in organic solvents commonly used in emulsifiable concentrates to be formulated as an aqueous solution or emulsifiable concentrate. Bendiocarb is also not sufficiently soluble in solvents generally used to make a solution for ultra low volume application; hitherto bendiocarb has not been available as a liquid formulation for ultra low volume application.

A useful liquid formulation of bendiocarb, especially for ultra low volume application, has now been discovered.

Accordingly, the invention provides a stable, pesticidal, liquid suspension of low volatility, comprising bendiocarb suspended in a chemically inert oil of low volatility and of low solubility for bendiocarb.

The invention provides also a process for preparing the suspension, which process comprises admixing the ingredients.

The invention also provides a method of combating pests at a locus infested or liable to be infested with them, which method comprises applying to the locus a pest-combating amount of the suspension.

The suspension, being liquid, avoids any problems of dustiness arising from a powder. The suspension is particularly useful as a ready-to-use formulation and especially useful for ultra low volume application.

A liquid formulation to be useful has to be stable to storage, i.e. the active ingredient must not undergo chemical change to remove the desired properties of the active ingredient and must not separate out and cause problems such as difficulty in measuring out the correct amount and applying a uniform amount of the active ingredient. The present suspension is surprisingly stable. Stability may be assessed in the laboratory by an accelerated storage test. Present suspensions have been found to be stable in such a test for at least 3 months, e.g. at least 6 months, at 40° C.

The suspension preferably exhibits non-Newtonian flow properties. Especially preferred is its being thixotropic. Simple agitation, e.g. a few gentle inversions of a can containing the suspension, makes the thixotropic material readily flowable.

The suspension, being liquid, can be poured out or readily measured out. It can be used straight from its container without further handling or dilution.

The suspension generally contains 5–700g, e.g. 5–500g, of bendiocarb per liter. If too much is contained, a highly viscous non-pourable paste is formed. Conveniently for storage, transport and use, the suspension contains 100–300g e.g. 150–300g of bendiocarb per liter.

The bendiocarb must be sufficiently finely divided. By being finely divided, the sedimentation velocity of the bendiocarb particles is reduced and they present a greater surface area per unit weight; hence they can be held in suspension better. So that also the suspension can pass through the usual equipment for ultra low volume application, the bendiocarb particles in the suspension are preferably substantially all less than 20 microns in largest dimension. Particle sizes in this specification are as measured under a microscope. The majority of the bendiocarb particles by weight are usually 0.05–20, e.g. 3–5, microns in largest dimension.

The oil carries the bendiocarb. Usually there is 300–996 ml, e.g. 500–900 ml, of the oil per liter of suspension. The oil must be chemically inert, i.e. it does not react chemically with the bendiocarb.

The volatility of the suspension depends on that of the oil. Both must be of low volatility, i.e. when 0.3 cubic centimeters of it is placed in a petri dish of diameter 5 cm, then after 7 hours storage in still air at 20° C., not more than 20% by weight evaporates; preferably, not more than 10% by weight evaporates, and especially between 0 and 5% by weight evaporates. Because of the low volatility, the bendiocarb particles in use remain associated with the oil, thus facilitating contact with the pest to be combated. The low volatility also makes the present formulation safer by being less liable to ignite and also by preventing the drift in air which would be liable to occur on application of a formulation containing a more volatile oil; the present oil cannot consist for instance of diesel oil. The present oil usually has a flash point greater than 100° C., preferably greater than 120° C. Usually its flash point is between 100° and 300° C., typically 130°–200° C.

The oil must be of low solubility for bendiocarb, i.e. its solubility for bendiocarb is below 10 g, preferably below 0.05 g, per liter of oil at 20° C. If the solubility is too high, crystal growth of the bendiocarb may occur on storage of the formulation.

The kinematic viscosity of the oil is usually between 0 and 100 centistokes, preferably from 5 to 25 centistokes, at 40° C.

The boiling point of the oil usually lies in the range 200°–400° C.

The oil can be an animal oil, a vegetable oil (e.g. rape seed oil or cotton seed oil), a mineral oil or a plasticizer oil (e.g. diisooctyl phthalate). The oil can be an ester, for example a glyceride or a phthalate (e.g. a phthalate plasticizer). Preferably, however, the oil is a hydrocarbon, preferably a paraffin oil, especially a highly paraffinic oil (e.g. at least 99% by weight of the oil being paraffinic). The presence of significant amounts of aromatic compounds may cause phytotoxicity problems if the formulation contacts plants. In addition, the solubility of bendiocarb in aromatic oils tends to be too high. Preferably the oil is a highly refined paraffin oil, being of technical or pharmaceutical quality. Suitable oils include Risella EL (from Shell Oil Company), Fyzol llE (from Fisons Limited) or Klearol (from Witco Chemical Corp). A mixture of oils may be employed.

A suspending agent may be present to help hold the bendiocarb in suspension, especially when lower concentrations of bendiocarb are employed. Preferably, the suspension contains 1–100 g of suspending agent per liter.

The suspending agent usually gives the formulation a gel structure, which causes the formulation to exhibit non-Newtonian, usually thixotropic, flow properties.

The suspending agent may be a natural, modified natural, or synthetic, material. The suspending agent is generally a swelling or non-swelling mineral clay, often organically modified to confer particular properties. The clays may be natural or synthetic.

The clays are preferably used in admixture with additives to secure their optimum properties. Suitable additives include (i) mixtures of lower alcohols and water, (ii) propylene carbonate, (iii) acetone, (iv) lower glycol ethers, or (v) gamma-butyrolactone. The additives may be present for instance as 10–50% by weight of the clay.

As natural, swelling clays, there may be used smectite minerals including smectite itself, montmorillonite, bentonite, hectorite, saponite, sauconite, vermiculite, nontronite, kaolinite, halloysite or illite, especially the first four. As non-swelling clays, there may be used attapulgite or sepiolite. As synthetic swelling clays, there may be used hectorite (e.g. Laponite RD or Laponite RDS, both from Laporte).

The suspending agent may be synthetic silica, e.g. pyrogenic silica or fine, precipitated, silica.

The suspending agent may be an organic derivative of castor oil or an inorganically modified derivative of castor oil.

The suspending agent may be a metal stearate, e.g. aluminium stearate.

A mixture of suspending agents may be employed.

A surface active agent is generally present in the formulation, to facilitate wetting of the solid phase into the oil phase, to disperse the particles once wetted, and as an aid to keep the formulation flowable, pourable and pumpable. The formulation usually contains 1–200 g, e.g. 1–100 g, of surface active agent per liter.

The term 'surface active agent' is used in the broad sense to include materials variously called emulsifying agents, dispersing agents and wetting agents. Such agents are well known in the pesticide art.

The surface active agents used may comprise anionic surface active agents, for example mono- or di-esters of phosphoric acid with fatty alcohol ethoxylates or with alkyl-phenol ethoxylates, salts of such esters, fatty alcohol sulphates such as sodium dodecyl sulphate, sodium octadecyl sulphate or sodium cetyl sulphate, ethoxylated fatty alcohol sulphates, ethoxylated alkylphenol sulphates, lignin sulphonates, petroleum sulphonates, alkyl-aryl sulphonates such as alkyl-benzene sulphonates or lower alkyl-naphthalene sulphonates, e.g. butyl-naphthalene sulphonate, salt of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates, e.g. the sodium sulphonate of dioctyl succinate.

The surface active agents may also comprise non-ionic agents, for example condensation products of fatty acid esters, fatty alcohols, fatty acid amides or fatty-, alkyl- or alkenyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols. By 'fatty' is meant herein hydrocarbon of 12–18 carbon atoms.

The surface active agents may also comprise cationic agents, for example alkyl and/or aryl-substituted quaternary ammonium compounds such as cetyl trimethylammonium bromide or ethoxylated tertiary fatty amines.

Non-ionic surface active agents are preferred. Outstanding surface active agents are condensation products with ethylene oxide. Particularly outstanding surface active agents are:

(A) Condensation products of alkyl- or alkenyl- substituted phenols with ethylene oxide, e.g. such products whose alkyl or alkenyl groups contain 6–18 carbon atoms and which contain 2–6 moles of ethylene oxide. Preferred such products are nonyl phenol-ethylene oxide condensates containing 2–6 moles, particularly 4 moles, of ethylene oxide, and especially polyoxyethylene oleylphenol;

(B) Condensation products of ethylene oxide with hydrocarbon of 12–18 carbon atom esters of polyhydric alcohol ethers, e.g. containing 2–25 moles of ethylene oxide, such as polyoxyethylene sorbitan oleate and/or laurate; or (C) Condensation products of hydrocarbon of 12–18 carbon atom alcohols with ethylene oxide, e.g. 2–6 moles of ethylene oxide.

A mixture of surface active agents may be employed.

Besides bendiocarb, the suspension may contain other compatible pesticides, e.g. herbicides, plant growth regulants, other insecticides or other acaricides.

The suspension can be prepared by admixing the ingredients. When a suspending agent is employed, it is preferred to apply a high amount of shear to it to disperse it and to invoke its properties. Preferably, the suspending agent is dispersed in at least some of the oil before admixing the bendiocarb therewith.

To use the suspension to combat pests, it can be diluted, for example with water or hydrocarbon e.g. diesel oil, and then applied, normally by spraying. Alternatively the suspension can be applied undiluted, normally by spraying. The suspension is especially useful for ultra low volume application, and particularly as a space spray, e.g. applied from aircraft or an ultra low volume aerosol generator. For spraying from aircraft, the suspension can be diluted with hydrocarbon to facilitate passage through the spray equipment.

The suspension can be used against public health and agricultural pests, especially public health pests. The pests are usually arthropods, especially insects. The suspension may be applied indoors, e.g. in buildings (for instance public buildings, houses, flats and warehouses), in aircraft or on ships, e.g. in food preparation or storage areas. It is preferably applied outdoors, however, e.g. in urban areas, rangelands or forests. It is particularly useful against stored product pests and especially flying insect pests such as mosquitoes, flies, grasshoppers, locusts or gypsy moths (*Porthetria dispar*).

The suspension is also useful against agricultural insect pests. Thus, it can be used on plants, land or the soil. The suspension may be used to dress seed, for example seeds of vegetables, notably brassicas, onions and beans, or cereals, notably wheat, barley, oats and maize. The dressed seed is protected against insects including coleoptera and diptera, for example wireworms (Agriotes Spp), pygmy beetle (Atomaria), collembola and millipedes, symphilids and flea beetles (Chaetocnema Spp). For use as a seed dressing, the suspension may contain an adhesive to facilitate adhesion of the active ingredient to the seed. The amount of adhesive in the suspension may be, for example, 5–50 g per liter.

When used indoors on surfaces, the suspension is usually employed at a rate of 10-1000 mg of bendiocarb per square meter. When used outdoors, e.g. at a locus where plants are growing or are to grow, the suspension is usually employed at a rate of ⅛-2, e.g. ¼-2, kg of bendiocarb per hectare. When used as a seed dressing, the suspension is usually employed at a rate of 0.1-28 g, preferably 0.25-10 g, of bendiocarb per kg of seed.

Preferably, the suspension is applied into the atmosphere, as a space spray. For this use, it is preferably applied at a rate of less than 5 liters of liquid per hectare (i.e. as an ultra low volume application), usually 10-5000, e.g. 20-5000, ml per hectare.

Remarkably small amounts of the suspension are required in order to be effective against pests.

The formulation can be applied by conventional equipment, e.g. conventional ultra low volume equipment. It is a feature of preferred formulations, like that of the following Example 1, that when used in commercial spraying equipment, the formulation can be left in the sprayer overnight without the need to flush the system through.

The invention is illustrated by the following Example.

EXAMPLE 1

The formulation consists, per liter, of:
Bendiocarb technical—to give bendiocarb: 250 g
Atlox 1045A (Atlas)—polyoxyethylene sorbitan oleate/laurate, surface active agent: 25 g
Geopon GO 11 (NL Industries)—organically modified montmorillonite clay, suspending agent: 25 g
Risella EL (Shell)—technical grade mineral oil: 750 ml The Atlox 1045A and Geopon GO 11 were dispersed in 450 ml of the Risella oil per liter of ultimate formulation, using the high speed mixer Silverson AXR for 30 minutes. The remaining Risella oil was then added and stirred in, using the same mixer. The bendiocarb was then dispersed in the mixture using the same mixer. Finally, the product was ball milled in a Dyno KDL mixer (from W Bachofen) to give a particle size of 0.5-5 microns in largest dimension by microscopic examination.

The viscosity of the freshly made formulation was 115,000 centipoises, measured at 20° C. on a Brookfield viscometer, model RVT, number 3 spindle, at 0.5 revolution per minute.

EXAMPLE 2

The formulation consists, per liter, of:
Bendiocarb technical, to give bendiocarb: 250 g
Triton X-207 (polyoxyethylene alkylphenol containing 20% dinonyl phenol, surface active agent): 100 g
Geopon GO-11 (NL Industries, organically modified montmorillonite clay, suspending agent): 10 g
Propylene carbonate: 3.3 g
Klearol (medicinal grade mineral oil): 690 ml 600 Ml of the Klearol per liter of the ultimate formulation were charged to an Attritor 1S ball mill. The Triton and then the bendiocarb were added, and the mixture was milled to a particle size less than 15 microns in largest dimension by microscopic examination. The Geopon was dispersed in the remaining Klearol using a turbine stirrer, and the propylene carbonate was added; the resulting liquor was passed through a Premier 84 laboratory colloid mill to give a stiff gel. The gel was added to the milled material in the Attritor ball mill, and the mixture milled to obtain a homogenous suspension.

The viscosity of the freshly made formulation, as measured as in Example 1 but with a number 2 spindle, was 10,000 centipoises.

EXAMPLE 3

Following the procedure of Example 2, formulations with the following content per liter were prepared:
Bendiocarb technical, to give bendiocarb: 250 g
Atlox 1045A (Atlas, polyoxyethylene sorbitan oleate/laurate, surface active agent): 20 g
Geopon GO 11 (NL Industries, organically modified montmorillonite clay, suspending agent): 20 g
Klearol (medicinal grade mmineral oil): 755 ml The viscosity of the freshly made formulations, as measured as in Example 1, was 45000-80000 centipoises.

EXAMPLE 4

The formulation of Example 1 was applied through a Micro-Gen aerosol generator ED2-20A in field trials in the United States of America against mosquitoes. The sprayer was conveyed at 16 kg per hour, and the insecticide was applied at the following rates, assuming an effective dispersal of 100 m from the spray route in assessing rates per ha:

| ml/min | g bendiocarb/min | g bendiocarb/ha |
|---|---|---|
| 53 | 13.3 | 5 |
| 74 | 18.5 | 7 |
| 98 | 24.4 | 9 |

Female mosquito adults, either bred from laboratory stock or collected in the field as larvae or pupae, were placed in disposable cylindrical bioassay cages 15 cm diameter × 4.5 cm deep with a fine nylon mosquito net with a 1.5 mm mesh at each end. These were suspended from brackets placed in the field so that the cage centres were 160 cm and 40 cm above ground in all tests. Three such brackets were set 15 m apart at 50 m from the spray route with another three sets at 100 m. Therefore 12 cages were exposed in each test. Four control (unsprayed) cages were held upwind from the spray. About 25 mosquitoes were placed in each cage, more or less depending on the numbers available. The cages were left in the field for 15 minutes after spraying in which time the mosquitoes either became moribund or remained healthy. Mortalities were recorded at 12 hours after exposure.

The *Culex quinquefasciatus* of field origin used in the tests is known to be resistant to malathion and naled.

The results are shown below

| | | Percentage Mortalities at 12 hours | | | | | |
|---|---|---|---|---|---|---|---|
| | | Control | 50 m | | 100 m | | Insect. |
| Females only | | (Untreated) | 160 cm | 40 cm | 160 cm | 40 cm | Rate ml/min |
| *Aedes aegypti* | L | 0 | 100 | 100 | 98 | 95 | 74 |
| *Aedes sollicitans* | F | 1 | 100 | 100 | 100 | 100 | 98 |
| | | 2 | 89 | 79 | 94 | 78 | 74 |
| *Aedes taeniorhynchus* | L | 1 | 93 | 98 | 98 | 100 | 74 |
| *Aedes triseriatus* | L | 2 | 98 | 77 | 92 | 50 | 74 |
| *Culex pipiens* | L | 7 | 100 | 100 | 100 | 100 | 74 |
| | | 2 | 100 | 99 | 95 | 83 | 53 |
| *Culex quinquefasciatus* | F | 0 | 100 | 95 | 91 | 52 | 98 |

-continued

| Females only | | Percentage Mortalities at 12 hours | | | | | |
|---|---|---|---|---|---|---|---|
| | | Control (Untreated) | 50 m | | 100 m | | Insect. Rate ml/min |
| | | | 160 cm | 40 cm | 160 cm | 40 cm | |
| Anopheles | L | 0 | 100 | 100 | 100 | 100 | 74 |

L = Laboratory Stock
F = Field Stock

Four series of air samples were taken at 5, 10, 25, 50 and 100 m from the spray route to measure the level of bendiocarb present in air when sprayed at the rate of 98 ml/min. Air was sampled at the rate of 4 liters/min for 5 minutes to coincide with the passing of the insecticide cloud. The mean concentration of insecticide in the air was 0.016 mg active ingredient per $m^3$ over the 5 minute sampling period, well below the industrial Threshold Limit Value Time Weighted Average over an 8 hour day or 40 hour working week of 0.2 mg active ingredient per $m^3$.

The formulation worked perfectly through the Micro-Gen sprayer. The formulation could be left in the sprayer overnight without needing to flush the system through.

EXAMPLE 5

The formulation of Example 3 was sprayed at a developing building site in the United States of America at a rate of 30 ml per minute from a sprayer mounted on a truck travelling at 16 km per hour, giving an effective insecticide swathe of at least 100 m. This rate is equivalent to 3 g bendiocarb per hectare. The control of mosquitoes *Culex quinquefasciatus* in cages was assessed, as was the control achieved by analogous treatment using malathion at the standard dose rate of 47 g malathion per hectare. The bendiocarb treatment gave 100% control while the malathion treatment gave 70% control.

The bendiocarb formulation did not kill larvae, and this is considered of major technical importance in not building up resistance.

EXAMPLE 6

The formulation of Example 3 was sprayed in the United States of America against *Aedes taeniorhynchus* (malathion resistant), *Culex nigrapalpus* and *Psorophora columbiae*. The sprayer delivered 120 ml per minute and travelled at 16 km per hour. Effective control of all the species was achieved.

EXAMPLE 7

The formulation of Example 3 was sprayed in the United States of America at 30 ml per minute from a sprayer travelling at 16 km per hour under erratic wind conditions against *Psorophora columbiae*. Effective control was achieved.

EXAMPLE 8

The formulation of Example 3 was sprayed from aircraft against grasshoppers late in their season in the United States of America. A dose of 150 g bendiocarb per ha gave 87% control. The standard melathion dose is 600 g melathion per ha, and the standard carbaryl dose is 680 g carbaryl per ha.

We claim:

1. A stable, pesticidal, liquid suspension of low volatility comprising 100–300 g of bendiocarb per liter of suspension, said bendiocarb having a particle size of less than 20 microns in largest dimension and being suspended in 300–996 ml per liter of suspension of a chemically inert oil, said oil having a solubility for bendiocarb below 0.05 g/liter of oil at 20° C., a flash point between 100° and 300° C., a kinematic viscosity between 0 and 100 centistokes at 40° C., a boiling point of 200° to 400° C., said suspension also comprising 1–200 g/liter of a surface active agent.

2. A suspension according to claim 1 containing 150–300 g of bendiocarb per liter.

3. A suspension according to claim 1 wherein the kinematic viscosity is from 5 to 25 centistokes at 40° C.

4. A suspension according to claim 1 wherein the oil is a paraffin oil.

5. A suspension according to claim 1 which contains 1–100 g per liter of suspension of a suspending agent to make the suspension thixotropic.

6. A composition which comprises a suspension according to claim 5 diluted with water or hydrocarbon suitable for spraying.

7. A method of combating pests at a locus infested or liable to be infested with them, which method comprises applying to the locus a pest-combating amount of the suspension claimed in claim 6.

8. A suspension according to claim 5 wherein the suspending agent is a montmorillonite clay.

9. A suspension according to claim 1 wherein the surface active agent is non-ionic.

10. A suspension according to claim 9 wherein the non-ionic surface active agent is a condensation product with ethylene oxide.

11. A suspension according to claim 10 wherein the non-ionic surface active agent is a condensation product of an alkyl- or alkenyl-substituted phenol with ethylene oxide.

12. A suspension according to claim 10 wherein the non-ionic surface active agent is a condensation product of ethylene oxide with an ester of a polyhydric alcohol ether with a hydrocarbon carboxylic acid of 12–18 carbon atoms.

13. A suspension according to claim 10 wherein the non-ionic surface active agent is a condensation product of ethylene oxide with a hydrocarbon alcohol of 12–18 carbon atoms.

14. A method of combating pests at a locus infested or liable to be infested with them, which method comprises applying to the locus a pest-combating amount of the suspension claimed in claim 1.

15. A method according to claim 14 wherein the application is outdoors.

16. A method according to claim 14 wherein 10–5000 ml are applied per hectare.

* * * * *